(12) United States Patent
Hirayama et al.

(10) Patent No.: US 12,366,569 B2
(45) Date of Patent: Jul. 22, 2025

(54) METHOD FOR DETECTING SLE

(71) Applicants: Keio University, Tokyo (JP); National University Corporation Tokai National Higher Education and Research System, Nagoya (JP)

(72) Inventors: Akiyoshi Hirayama, Tsuruoka (JP); Tomoyoshi Soga, Tsuruoka (JP); Shoichi Maruyama, Nagoya (JP); Shinichi Akiyama, Nagoya (JP)

(73) Assignees: Keio University, Tokyo (JP); National University Corporation National Higher Education and Research System, Nagoya (JP)

( * ) Notice: Subject to any disclaimer, the term of this patent is extended or adjusted under 35 U.S.C. 154(b) by 953 days.

(21) Appl. No.: 17/417,640

(22) PCT Filed: Dec. 26, 2019

(86) PCT No.: PCT/JP2019/051066
§ 371 (c)(1),
(2) Date: Jun. 23, 2021

(87) PCT Pub. No.: WO2020/138260
PCT Pub. Date: Jul. 2, 2020

(65) Prior Publication Data
US 2022/0120730 A1    Apr. 21, 2022

(30) Foreign Application Priority Data
Dec. 26, 2018 (JP) ................................. 2018-242371

(51) Int. Cl.
*G01N 33/493* (2006.01)

(52) U.S. Cl.
CPC ....... *G01N 33/493* (2013.01); *G01N 2560/00* (2013.01); *G01N 2800/104* (2013.01); *G01N 2800/52* (2013.01)

(58) Field of Classification Search
CPC ............. G01N 33/493; G01N 33/5308; G01N 2800/104; G01N 2800/52; G01N 2800/347; G01N 33/564
USPC ........................................................ 436/506
See application file for complete search history.

(56) References Cited

U.S. PATENT DOCUMENTS 11,279,728 B2 *    3/2022    Almo ..................... C07H 19/10

OTHER PUBLICATIONS

Ahmed et al., DFT Study on the Conformational and Vibrational Properties of 3'-Deoxycytidine and Its Analogues, (2013), International Journal of Chemistry; vol. 5, No. 2; 2013, 68-85. (Year: 2013).*
Shinichi, A. et al., "Novel urine metabolite in human as a new differential diagnosis biomarker for lupus nephritis", Glomerular Diseases: Immunology, Inflammation, Session Information, Abstract: FR-PO843, Nov. 8, 2019.
Tritten, L. et al., "Metabolic profiling framework for discovery of candidate diagnostic markers of malaria", Scientific Reports, vol. 3, No. 2769, pp. 1-7, (2013).

* cited by examiner

*Primary Examiner* — Gregory S Emch
*Assistant Examiner* — Omar Ramadan
(74) *Attorney, Agent, or Firm* — EVAN LAW GROUP LLC

(57) ABSTRACT

An object of the present invention is to provide a method capable of detecting whether a subject has systemic lupus erythematosus (preferably nephrotic syndrome) with high accuracy without performing a renal biopsy, a biomarker for carrying out such detection, and the like. The concentration of 3',4'-didehydro-3'-deoxycytidine in urine collected from a test subject is measured, and this concentration is compared with a reference concentration for control, which allows to detect whether the above-mentioned test subject has systemic lupus erythematosus (preferably lupus nephritis) with high accuracy.

9 Claims, 8 Drawing Sheets

[Fig. 1]
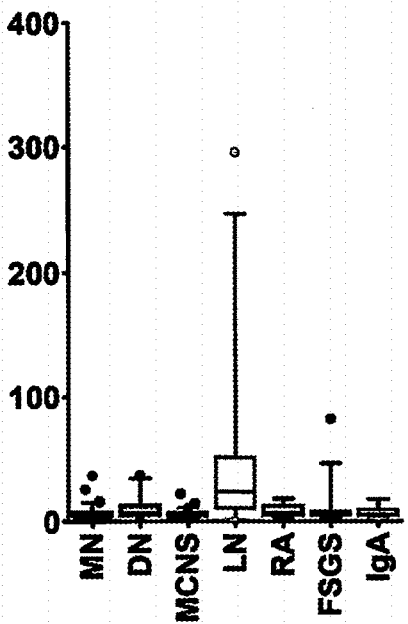
[Fig. 2]
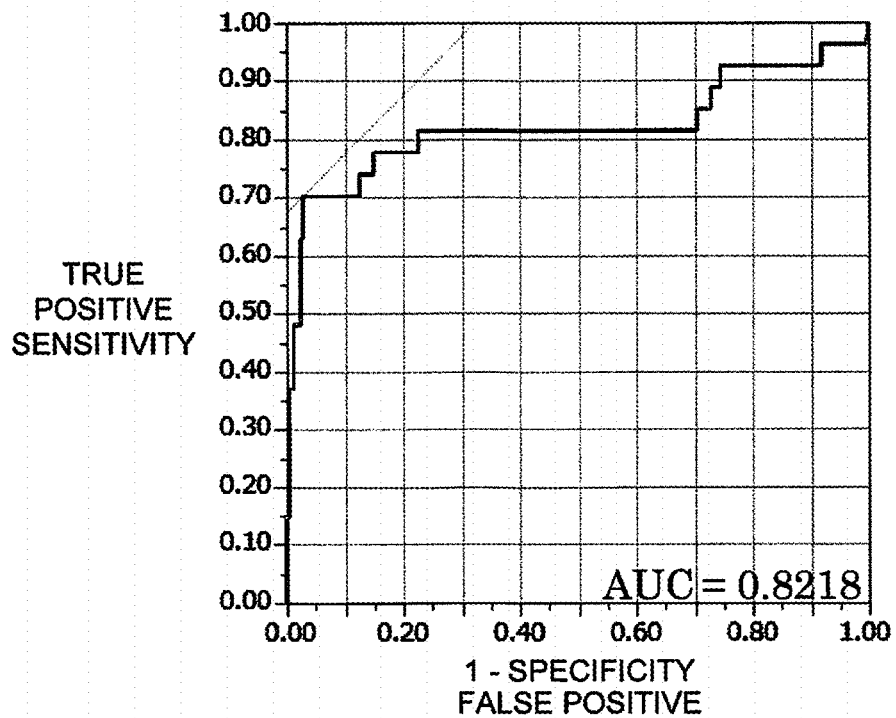

CU040 (PARTIALLY PURIFIED)

[Fig. 4]
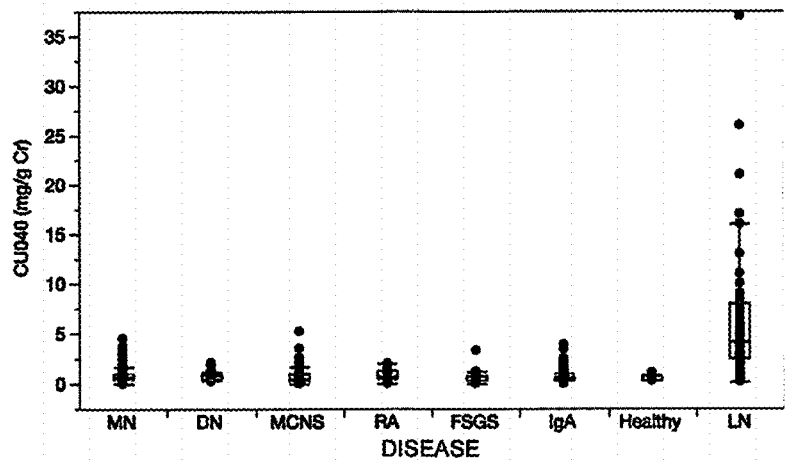
[Fig. 5]
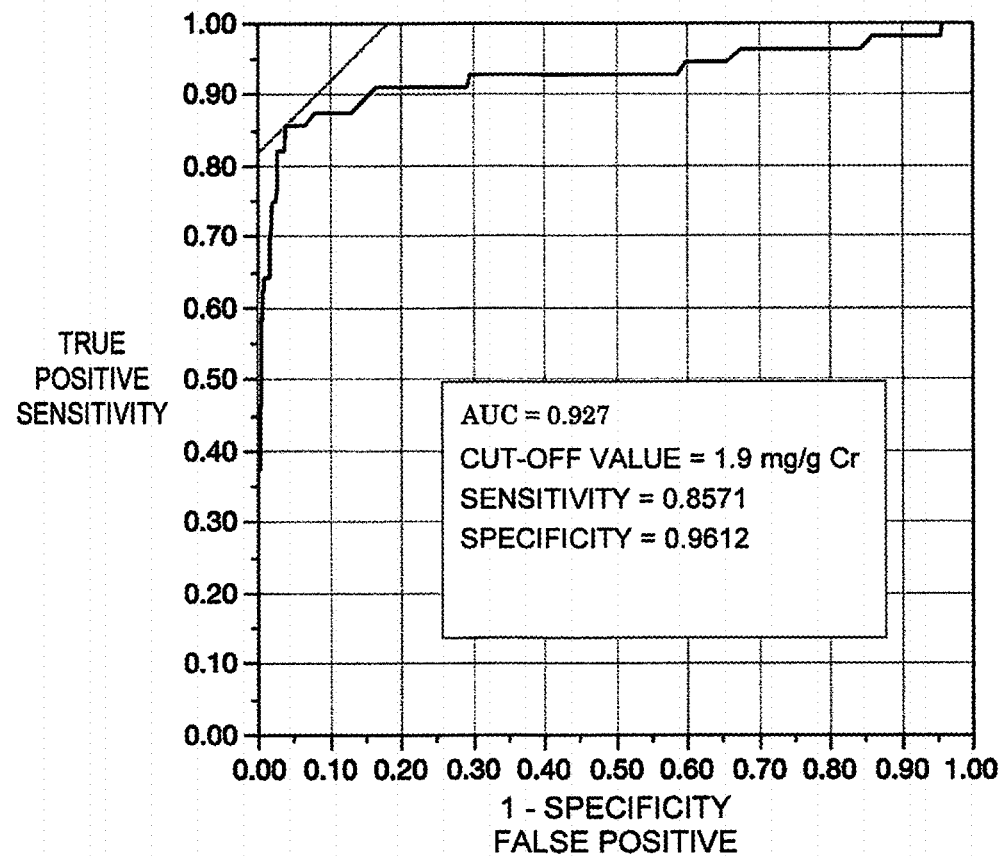

[Fig. 6]
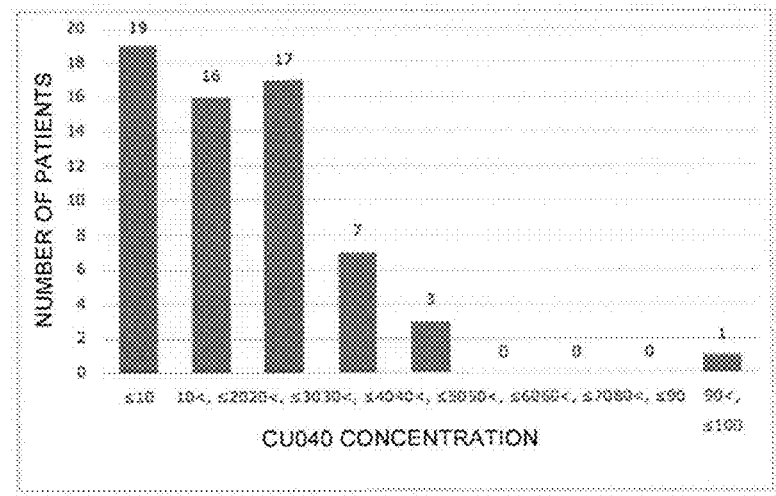
MEDIAN 18 [QUARTILE: 9-28]
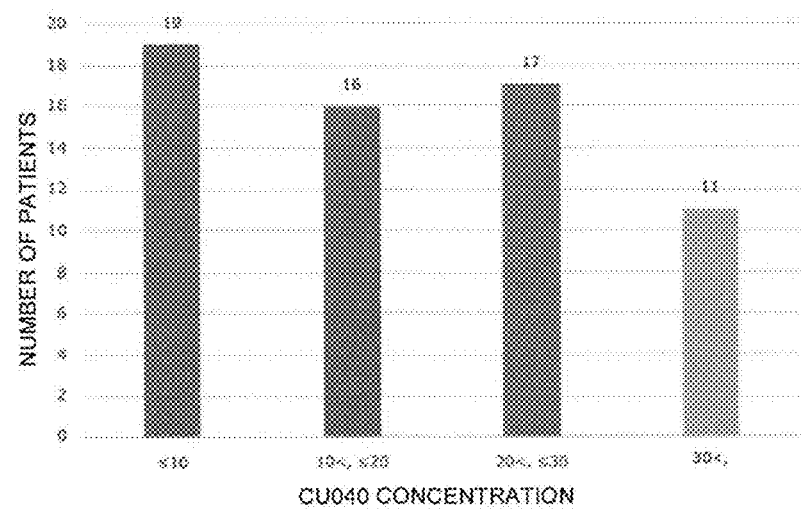
EXAMINATION OF CU040 CONCENTRATION
BY DIVIDING IT INTO 4 RANGES

METHOD FOR DETECTING SLE

TECHNICAL FIELD

The present invention relates to a method for detecting or predicting the prognosis of systemic lupus erythematosus, a biomarker for detecting or predicting the prognosis of systemic lupus erythematosus, a kit for detecting or predicting the prognosis of systemic lupus erythematosus, and the like.

BACKGROUND ART

Systemic lupus erythematosus (SLE) is an autoimmune disease characterized by systemic inflammatory lesions caused by the deposition of immune complexes such as DNA-anti-DNA antibodies in tissues. In SLE, systemic inflammation such as fever and general malaise, and damage to various organs including the joints, nervous system, blood, skin, kidneys, gastrointestinal tract and lungs occur at once or over time. SLE often takes a chronic course, with repeated remissions and exacerbations. Since the type, course and extent of SLE symptoms vary from patient to patient, SLE is more difficult to be diagnosed than other diseases. The renal disorder caused by SLE is referred to as lupus nephritis, and whether or not lupus nephritis develops and the severity of the symptoms of lupus nephritis at the start of treatment are factors which affect the life prognosis of SLE patients. Since a delay in SLE diagnosis results in a worse prognosis, SLE is a disease in which early diagnosis and early treatment are important. Currently, SLE is diagnosed by considering a multitude of factors including the presence or absence of SLE-related symptoms and the presence or absence of antinuclear antibodies in the blood, and there is currently no single conclusive indicator. Therefore, there is still a demand for a novel detection method leading to early diagnosis of SLE.

Meanwhile, nephrotic syndrome is a general term for renal diseases characterized by a large amount of urinary protein and hypoproteinemia, and its underlying causes are diverse, including primary glomerular diseases, collagen diseases, and metabolic diseases. The affected age ranges widely as well, from children to the elderly. The mechanisms leading to the onset of nephrotic syndrome are various. Once developed, the disease often lasts for a long time, and many cases are resistant to treatment.

Currently, as criteria for diagnosing adult nephrotic syndrome, two criteria have been established as essential conditions: (i) urinary protein of 3.5 g or more per day, and (ii) serum albumin concentration of 3.0 g/dL or less. As additional reference conditions, (iii) edema and (iv) dyslipidemia are also widely used. However, there are various forms of nephrotic syndrome, and typical examples include minimal change nephrotic syndrome (MCNS), membranous nephropathy (MN), diabetic nephropathy (DN), focal segmental glomerulosclerosis (FSGS), lupus nephritis (LN), IgA nephropathy (IgA), and renal amyloidosis (RA). Since the method of treatment to administer varies with the different forms of nephrotic syndrome, it is clinically very important to accurately diagnose the form of nephrotic syndrome.

Currently, renal biopsy is required not only for the definitive diagnosis of the form of nephrotic syndrome but also for the definitive diagnosis of renal diseases such as nephritis and nephrotic syndrome. However, since renal biopsy is a highly invasive test associated with a risk of bleeding, it is often not possible to perform a renal biopsy in patients whose general condition has deteriorated or in elderly patients. For example, diabetic nephropathy and nephrosclerosis are usually diagnosed by clinical speculation without performing a renal biopsy. When renal biopsy cannot be performed in such manner, the problem is that it becomes difficult to diagnose the disease, assess the pathological condition, and select an appropriate treatment method. Therefore, a method capable of identifying renal disease and the form thereof with high accuracy and minimal invasion, without performing a highly invasive renal biopsy is of great clinical value. For example, Patent Document 1 discloses a method of using human megalin in urine as a marker of renal disorder, and Patent Document 2 discloses a method of using a combination of specific metabolites such as creatinine and aspartic acid in blood as markers for differentiating diabetic nephropathy.

However, it was previously unknown that whether a subject has systemic lupus erythematosus (preferably lupus nephritis) can be detected with high accuracy using the concentration of 3',4'-didehydro-3'-deoxycytidine in urine as an indicator.

PRIOR ART DOCUMENTS

Patent Documents

Patent Document 1: Japanese Patent No. 5694145
Patent Document 2: Japanese Patent No. 6128631

SUMMARY OF THE INVENTION

Object to be Solved by the Invention

An object of the present invention is to provide a method capable of detecting whether a subject has systemic lupus erythematosus (preferably lupus nephritis) with high accuracy and without performing a renal biopsy, a biomarker for detecting systemic lupus erythematosus (preferably lupus nephritis), and the like.

Means to Solve the Object

In order to solve the above object, the present inventors have conducted a metabolome analysis using urine samples of healthy individuals and patients with seven different forms of nephrotic syndrome, and found that 3',4'-didehydro-3'-deoxycytidine (also referred to as ddh-Cytidine or ddh-C) is a biomarker capable of detecting whether the form of nephrotic syndrome is lupus nephritis with high accuracy. Since lupus nephritis is a renal disorder caused by systemic lupus erythematosus, detecting lupus nephritis is at the same time detecting systemic lupus erythematosus. In addition, the present inventors have also confirmed that the concentration of 3',4'-didehydro-3'-deoxycytidine in the urine of healthy individuals is extremely low, and that 3',4'-didehydro-3'-deoxycytidine is contained in the urine of systemic lupus erythematosus patients without lupus nephritis. Thereby, the present inventors have completed the present invention.

That is, the present invention relates to:
(1) a method for detecting systemic lupus erythematosus, comprising:
   (a) a step of measuring the concentration of 3',4'-didehydro-3'-deoxycytidine in urine collected from a test subject; and
   (b) a step of comparing the concentration of 3',4'-didehydro-3'-deoxycytidine measured in step (a) with a reference concentration for control, wherein a concentration of 3',4'-didehydro-3'-deoxycytidine measured in the step (a) higher than the reference concentration for control indicates a strong possibility that the test subject has systemic lupus erythematosus;

(2) the detection method according to the above (1), wherein a concentration of 3',4'-didehydro-3'-deoxycytidine measured in step (a) 1.2 times or more higher than the reference concentration for control indicates a strong possibility that a test subject has systemic lupus erythematosus;

(3) the detection method according to the above (1) or (2), wherein the reference concentration for control is the concentration of 3',4'-didehydro-3'-deoxycytidine in urine collected from a patient with nephrotic syndrome of a form other than lupus nephritis or from a healthy individual;

(4) the detection method according to any one of the above (1) to (3), wherein the test subject is a patient with nephrotic syndrome and the systemic lupus erythematosus is lupus nephritis;

(5) a biomarker for detecting systemic lupus erythematosus, consisting of 3',4'-didehydro-3'-deoxycytidine;

(6) the biomarker according to the above (5), wherein the concentration of the biomarker in urine collected from a test subject is higher than the concentration of the biomarker in urine collected from a patient with nephrotic syndrome of a form other than lupus nephritis or from a healthy individual;

(7) the biomarker according to the above (5) or (6), wherein the test subject is a patient with nephrotic syndrome and the systemic lupus erythematosus is lupus nephritis;

(8) a method for predicting the prognosis of systemic lupus erythematosus, comprising (A) a step of measuring the concentration of 3',4'-didehydro-3'-deoxycytidine in urine collected from a patient with systemic lupus erythematosus, wherein the prognosis of the patient with systemic lupus erythematosus is predicted to be good when the concentration of 3',4'-didehydro-3'-deoxycytidine measured in the step (A) is high;

(9) a biomarker for predicting the prognosis of systemic lupus erythematosus, consisting of 3',4'-didehydro-3'-deoxycytidine; and

(10) a kit for detecting or predicting the prognosis of systemic lupus erythematosus, comprising 3',4'-didehydro-3'-deoxycytidine as an internal standard substance for a mass spectrometer.

Effect of the Invention

According to the present invention, a method capable of detecting whether a subject has systemic lupus erythematosus (preferably nephrotic syndrome) with high accuracy and without performing a renal biopsy, a biomarker for detecting systemic lupus erythematosus (preferably nephrotic syndrome), and the like can be provided.

BRIEF DESCRIPTION OF DRAWINGS

FIG. 1 is a diagram showing the results of measuring the urinary concentration of CU040 (3',4'-didehydro-3'-deoxycytidine) in the groups of each form of nephrotic syndrome. The vertical axis represents the peak intensities of CU040, and the horizontal axis represents the groups of each form of nephrotic syndrome. MN stands for membranous nephropathy, DN for diabetic nephropathy, MCNS for minimal change nephrotic syndrome, LN for lupus nephritis, RA for renal amyloidosis, FSGS for focal segmental glomerulosclerosis, and IgA for IgA nephropathy. In each box plot, the lower end of the whiskers represents the 5th percentile, the bottom edge of the box represents the 25th percentile, the partition line in the box represents the 50th percentile, the top edge of the box represents the 75th percentile, and the upper end of the whiskers represents the 95th percentile of the group's measured values. In each group, the measured values of the samples having a concentration higher than the 95th percentile and the measured values of the samples having a concentration lower than the 5th percentile are indicated by dots in the graph of FIG. 1.

FIG. 2 is a diagram showing a ROC curve created based on the results of FIG. 1. The vertical axis represents the "sensitivity" (true positive rate), and the horizontal axis represents "1–specificity" (false positive rate).

FIGS. 3A, 3B and 3C show the spectrum of a synthetic product of 3',4'-didehydro-3'-deoxycytidine ("KAH51-57"), and FIGS. 3D, 3E and 3F show the spectrum of CU040.

FIG. 4 is a diagram showing the results of measuring the urinary concentration of CU040 (3',4'-didehydro-3'-deoxycytidine) in the groups of each form of nephrotic syndrome and in the group of healthy individuals. The vertical axis represents the urinary CU040 concentration (mg/g Cr) and the peak intensities of CU040, and the horizontal axis represents each group. MN stands for membranous nephropathy, DN for diabetic nephropathy, MCNS for minimal change nephrotic syndrome, RA for renal amyloidosis, FSGS for focal segmental glomerulosclerosis, IgA for IgA nephropathy, Healthy for healthy individuals, and LN for lupus nephritis. In each box plot, the lower end of the whiskers represents the 5th percentile, the bottom edge of the box represents the 25th percentile, the partition line in the box represents the 50th percentile, the top edge of the box represents the 75th percentile, and the upper end of the whiskers represents the 95th percentile of the group's measured values.

FIG. 5 is a diagram showing a ROC curve created based on the results of FIG. 4. The vertical axis represents the "sensitivity" (true positive rate), and the horizontal axis represents "1–specificity" (false positive rate).

FIG. 6 is a diagram showing the CU040 concentration distribution in the urine of patients with nephrotic syndrome. The upper graph shows the number of patients with nephrotic syndrome at nine levels of CU040 concentration, and the lower graph shows the number of patients with nephrotic syndrome at four levels of CU040 concentration. In the upper graph, "≤10" indicates a CU040 concentration range of less than 10 mg/g Cr, "10<, ≤20" indicates the range of 10 to 20 mg/g Cr, "20<, ≤30" the range of 20 to 30 mg/g Cr, "30<, ≤40" the range of 30 to 40 mg/g Cr, "40<, ≤50" the range of 40 to 50 mg/g Cr, "50<, ≤60" the range of 50 to 60 mg/g Cr, "60<, ≤70" the range of 60 to 70 mg/g Cr, "70<, ≤80" the range of 70 to 80 mg/g Cr, "80<, ≤90" the range of 80 to 90 mg/g Cr, and "90<, ≤100" the range of 90 to 100 mg/g Cr, respectively. Moreover, in the lower graph, "≤10" indicates a CU040 concentration range of less than 10 mg/g Cr, "10<, ≤20" the range of 10 to 20 mg/g Cr, "20<, ≤30" the range of 20 to 30 mg/g Cr, and "30<" the range of 30 mg/g Cr or more, respectively.

MODE OF CARRYING OUT THE INVENTION

Figure 3A:
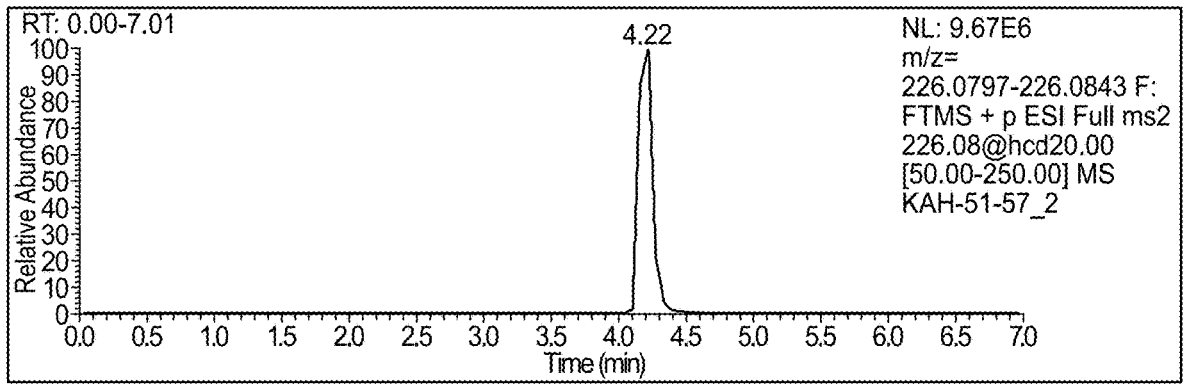
FIGS. 3A, 3B, 3C, 3D, 3E and 3F collectively are a diagram showing a tandem mass spectrum by nuclear magnetic resonance.
Figure 3B:
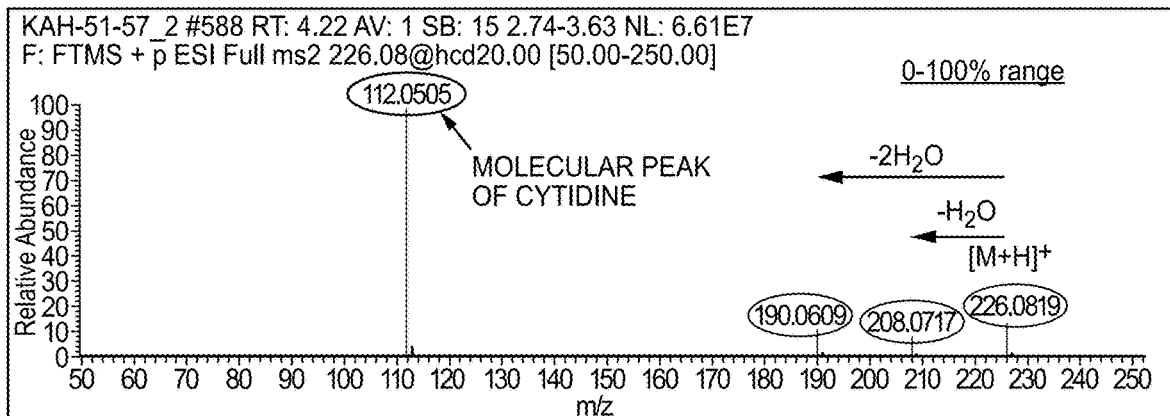
Figure 3C:
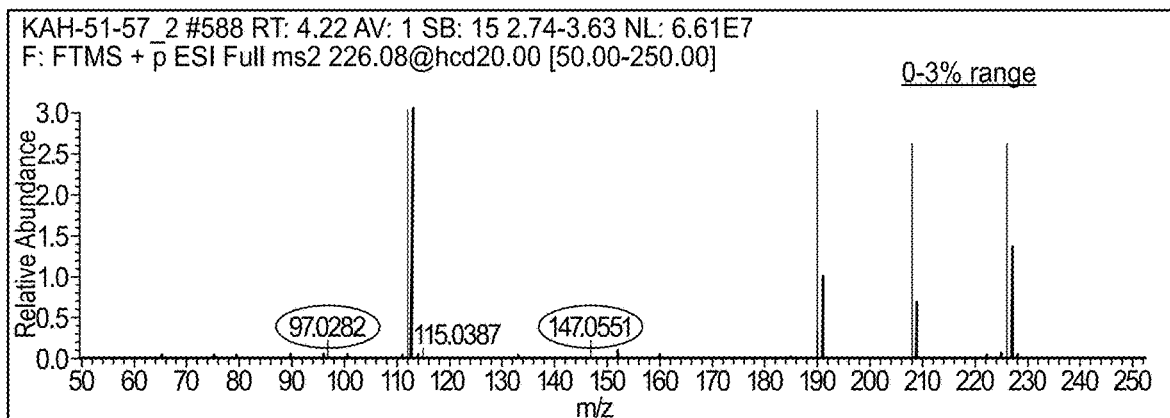
Figure 3D:
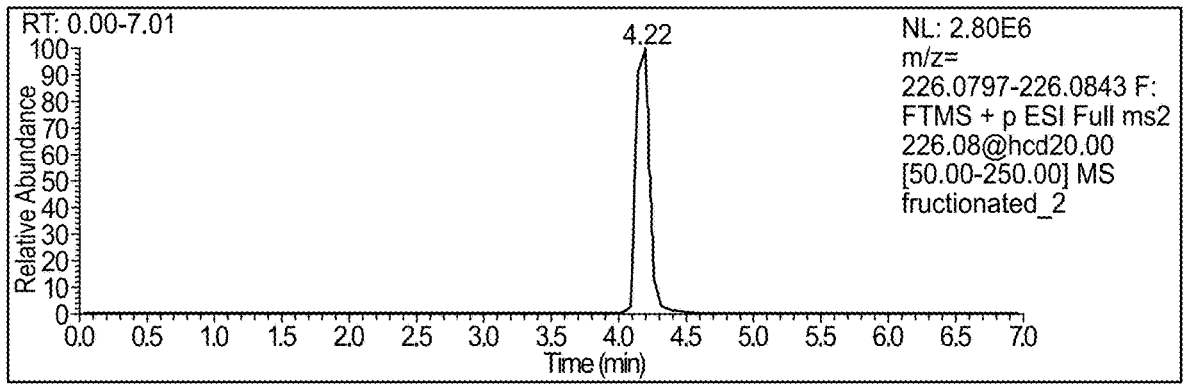
Figure 3E:
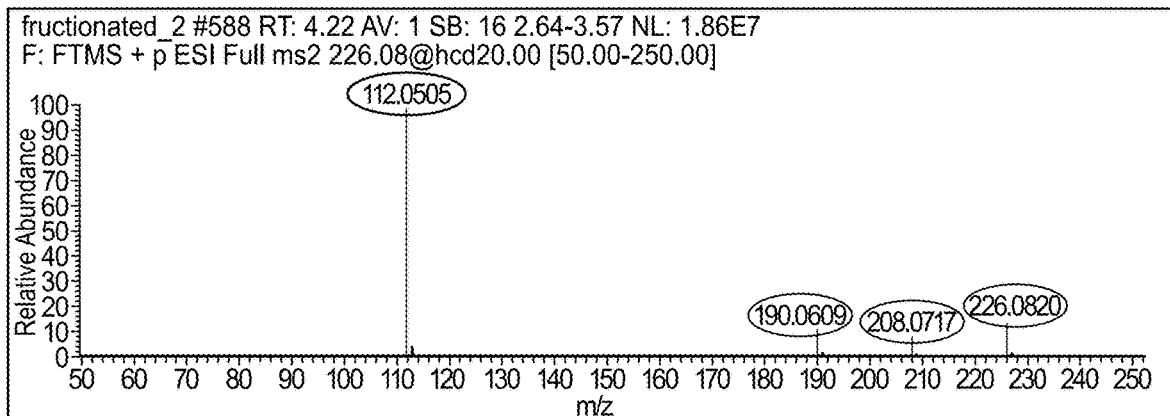
Figure 3F:
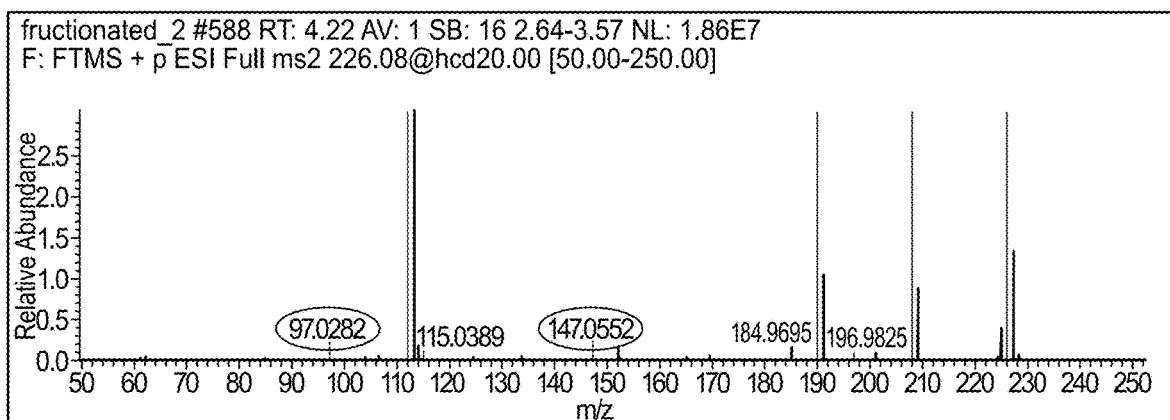

The present invention includes embodiments such as:
[1] a method for detecting systemic lupus erythematosus (hereinafter, also indicated as the "detection method of the present invention"), comprising:
  (a) a step of measuring the concentration of 3',4'-didehydro-3'-deoxycytidine in urine collected from a test subject; and
  (b) a step of comparing the concentration of 3',4'-didehydro-3'-deoxycytidine measured in step (a) with a reference concentration for control,
  wherein a concentration of 3',4'-didehydro-3'-deoxycytidine measured in the step (a) higher than the reference concentration for control indicates a strong possibility that the test subject has systemic lupus erythematosus;
[2] a biomarker for detecting systemic lupus erythematosus (hereinafter, also indicated as the "biomarker for detection of the present invention"), consisting of 3',4'-didehydro-3'-deoxycytidine;
[3] a method for predicting the prognosis of systemic lupus erythematosus (hereinafter, also indicated as the "method for prognosis prediction of the present invention"), comprising (A) a step of measuring the concentration of 3',4'-didehydro-3'-deoxycytidine in urine collected from a patient with systemic lupus erythematosus, wherein the prognosis of the patient with systemic lupus erythematosus is predicted to be good when the concentration of 3',4'-didehydro-3'-deoxycytidine measured in the step (A) is high; [3] a biomarker for predicting the prognosis of a patient with systemic lupus erythematosus (hereinafter, also indicated as the "biomarker for prognosis prediction of the present invention"), consisting of 3',4'-didehydro-3'-deoxycytidine; and
[4] a kit for detecting or predicting the prognosis of systemic lupus erythematosus (hereinafter, also indicated as the "kit of the present invention"), comprising 3',4'-didehydro-3'-deoxycytidine as an internal standard substance for a mass spectrometer. In the present description, unless otherwise specified, the "concentration" means the concentration of 3',4'-didehydro-3'-deoxycytidine in urine. Moreover, in the present description, "detecting whether a test subject has systemic lupus erythematosus" preferably includes "detecting whether a test subject has lupus nephritis", and more preferably includes "detecting whether the form of nephrotic syndrome is lupus nephritis when a test subject is a patient with nephrotic syndrome". Furthermore, in the present description, "the possibility that a test subject has systemic lupus erythematosus" preferably includes "the possibility that a test subject has lupus nephritis", and more preferably includes "the possibility that the form of nephrotic syndrome is lupus nephritis when a test subject is a patient with nephrotic syndrome".

(Detection Method of the Present Invention)

The detection method of the present invention is a method for detecting whether a test subject has systemic lupus erythematosus. The detection method of the present invention is not particularly limited as long as it is a method comprising:
  (a) a step of measuring the concentration of 3',4'-didehydro-3'-deoxycytidine in urine collected from a test subject; and
  (b) a step of comparing the concentration of 3',4'-didehydro-3'-deoxycytidine measured in step (a) with a reference concentration for control,
  wherein a concentration of 3',4'-didehydro-3'-deoxycytidine measured in step (a) higher than the reference concentration for control indicates a strong possibility that the test subject has systemic lupus erythematosus. The detection method of the present invention is a method for assisting doctors in diagnosing the possibility that a test subject has systemic lupus erythematosus, and does not include the diagnostic action of a doctor.

(Biomarker of the Present Invention)

The biomarker of the present invention is a biomarker for detecting whether a test subject has systemic lupus erythematosus. The biomarker of the present invention is not particularly limited as long as it is a biomarker for detecting systemic lupus erythematosus, consisting of 3',4'-didehydro-3'-deoxycytidine. This biomarker has a concentration in the urine collected from a patient with a nephrotic syndrome as lupus nephritis that is higher than the concentration of the biomarker in the urine collected from a patient with nephrotic syndrome of a form other than lupus nephritis.

The structural formula of 3',4'-didehydro-3'-deoxycytidine is shown below.

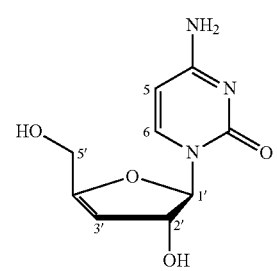

[Formula 1]

(Method for Prognosis Prediction of the Present Invention)

The method for prognosis prediction of the present invention is a method for predicting the possibility that a target patient with systemic lupus erythematosus will experience remission after an immunosuppressive treatment. The method for prognosis prediction of the present invention is not particularly limited as long as it is a method comprising (A) a step of measuring the concentration of 3',4'-didehydro-3'-deoxycytidine in the urine collected from a patient with systemic lupus erythematosus, and which predicts that the prognosis of the patient with systemic lupus erythematosus is good when the concentration of 3',4'-didehydro-3'-deoxycytidine measured in the step (A) is high. The method for prognosis prediction of the present invention is a method for assisting doctors in predicting the possibility of remission of a patient with systemic lupus erythematosus, and does not include the diagnostic action of a doctor.

(Biomarker for Prognosis Prediction of the Present Invention)

The biomarker for prognosis prediction of the present invention is a biomarker for predicting the prognosis of a patient with systemic lupus erythematosus. The biomarker of the present invention is not particularly limited as long as it is a biomarker for predicting the prognosis of a patient with systemic lupus erythematosus, consisting of 3',4'-didehydro-3'-deoxycytidine. This biomarker for prognosis prediction is present in higher concentrations in the urine collected from patients with systemic lupus erythematosus having a good prognosis.

(Systemic Lupus Erythematosus)

In the present description, "systemic lupus erythematosus" means a condition which falls under the diagnostic criteria revised in 1997 by the American College of Rheumatology (ACR) or the diagnostic criteria of 2012 by the Systemic Lupus International Collaborating Clinics (SLICC).

The above diagnostic criteria for SLE by the ACR classify as SLE a condition which satisfies four or more of the following items <1> to <11>. However, the symptomatic periods of these four or more items do not need to be the same.

<1> Facial erythema
<2> Discoid lupus
<3> Photosensitivity
<4> Mouth ulcer (painless and developed in the oral cavity or nasopharynx)
<5> Arthritis (non-destructive on two or more joints)
<6> Serositis (pleurisy or pericarditis)
<7> Renal lesions (persistent proteinuria of 0.5 g/day or more or development of cellular casts)
<8> Neurological lesions (seizures or mental disorders)
<9> Hematological abnormalities (hemolytic anemia, leukopenia of 4000/mm$^3$ or less, lymphopenia of 1500/mm$^3$ or less, or thrombocytopenia of 100,000/mm$^3$ or less)
<10> Immunological abnormalities (positive for anti-double-stranded DNA antibodies, positive for anti-Sm antibodies or positive for antiphospholipid antibodies (anti-cardiolipin antibodies, lupus anticoagulant, false positive reaction for syphilis))
<11> Positive for antinuclear antibodies The above diagnostic criteria by SLICC classify as SLE when four or more criteria (however, the four or more criteria include at least one immunological criterion) of the following seventeen criteria (that is, the following eleven clinical criteria and the following six immunological criteria) are satisfied; or when the test for antinuclear antibodies or anti-double-stranded DNA antibodies is positive and biopsy-proven lupus nephritis is present.

Clinical Criteria
<1> Acute cutaneous lupus
<2> Chronic cutaneous lupus
<3> Oral ulcer
<4> Non-scarring alopecia
<5> Synovitis
<6> Serositis (either pleurisy or pericarditis)
<7> Renal lesions (either urinary protein of 0.5 g/day or more or red blood cell casts)
<8> Neurological lesions (seizures, psychosis, mononeuropathy multiplex, myelitis, peripheral and central nervous system disorders, acute confusional state)
<9> Hemolytic anemia
<10> Leukopenia (<4,000/mm$^3$), or lymphopenia (<4,000/mm$^3$)
<11> Thrombocytopenia (<100,000/mm$^3$)

Immunological Criteria
<1> Positive for antinuclear antibodies
<2> Positive for anti-double-stranded DNA antibodies (exceeding twice the reference value with the ELISA method)
<3> Positive for anti-Sm antibodies
<4> Positive for antiphospholipid antibodies
<5> Low complement (C3, C4, CH50)
<6> Positive for direct Coombs test (no hemolytic anemia)

(Lupus Nephritis)

In the present description, "lupus nephritis" means the renal disorder associated with systemic lupus erythematosus (SLE). SLE is an autoimmune disease that can affect the entire body, and produces tissue damage caused by immune complex formation and complement. The location of tissue damage varies from case to case, and the damage can occur in various organs such as the kidneys, skin, lungs, and brain. As diagnostic criteria for SLE, for example, Updating the American College of Rheumatology revised criteria (1997) and The systemic lupus international collaborating clinics classification criteria for systemic lupus erythematosus (2012) are known.

In lupus nephritis, glomerulonephritis predominantly occurs, but vasculitis, interstitial nephritis, and the like can also occur. Lupus nephritis includes minimal mesangial lupus nephritis, mesangial proliferative lupus nephritis, focal lupus nephritis, diffuse lupus nephritis, membranous lupus nephritis and advanced sclerosing lupus nephritis, especially diffuse lupus nephritis. Symptoms of lupus nephritis include, for example, proteinuria and swelling. As lupus nephritis progresses, renal function declines, which may lead to renal failure. The diagnosis or classification of lupus nephritis can be based on, for example, the 2003 International Society of Nephrology (ISN) Classification of lupus nephritis or the ACR (American College of Rheumatology) clinical practice guidelines for lupus nephritis (2012).

(Nephrotic Syndrome)

In the present description, "nephrotic syndrome" means, in an adult (15 years old or older), a condition in which (i) urinary protein is 3.5 g or more per day, and (ii) serum albumin concentration is 3.0 g/dL or less, and in children (under 15 years old), a condition in which (i) urinary protein is 40 mg/hour/m$^2$ or more in urine collected at night, or the urinary protein/creatinine ratio is 2.0 g/g Cr or more in the first morning urine and (ii) serum albumin concentration is 2.5 g/dL or less. For nephrotic syndrome in children, the following criteria may be used instead of the criteria described above.

(i) Urinary protein is 3.5 g or more or 0.1 g/kg or more per day for three consecutive days or more, or the urinary protein in the first morning urine is 300 mg/mL or more for three consecutive days or more, and (ii) Total serum protein level is 6.0 g/100 mL or less for those aged 1 year old or older and under 15 years old, 5.5 g/100 mL or less for those under 1 year old, and serum albumin level is 3.0 g/100 mL or less for those aged 1 year old or older and under 15 years old, 2.5 g/100 mL or less for those under 1 year old.

(Test Subject)

In the present description, the term "test subject" is not particularly limited regarding the age, sex, presence or absence of disease, and the like, as long as it is a human being, but preferably includes a human who has not received a definitive diagnosis of systemic lupus erythematosus, and a human who has not received a definitive diagnosis of lupus nephritis, since it is highly significant for applying the detection method of the present invention. The above-mentioned human who has not received a definitive diagnosis of systemic lupus erythematosus is not particularly limited as long as it is a human who has not received a definitive diagnosis of systemic lupus erythematosus, and includes a human who is suspected to have systemic lupus erythematosus, a human who is not particularly suspected to have systemic lupus erythematosus, a human who has received a definitive diagnosis of nephrotic syndrome, a human who has not received a definitive diagnosis of nephrotic syndrome, a human who is suspected to have nephrotic syndrome, and a human who is not particularly suspected to have nephrotic syndrome. Moreover, the above-mentioned human who has not received a definitive diagnosis of lupus nephritis is not particularly limited as long as it is a human who has not received a definitive diagnosis of lupus nephritis, and includes a human who is suspected to have lupus nephritis, a human who is not particularly suspected to have lupus nephritis, a human who has received a definitive diagnosis of nephrotic syndrome, a human who has not received a definitive diagnosis of nephrotic syndrome, a human who is suspected to have nephrotic syndrome, and a human who is not particularly suspected to have nephrotic syndrome.

(Step (a) in Detection Method of the Present Invention)

The above step (a) is not particularly limited as long as it is a step of measuring the concentration of 3',4'-didehydro-3'-deoxycytidine in urine collected from a test subject. The concentration of 3',4'-didehydro-3'-deoxycytidine can be measured by preparing a urine sample for analysis from urine (that is, a urine sample) collected from a test subject, and using a publicly known method capable of specifically detecting 3',4'-didehydro-3'-deoxycytidine, for example, mass spectrometry. This mass spectrometry refers to a measurement method using a mass spectrometer capable of detection by converting a urine sample into gaseous ions (ionization) using an ion source, then in the analysis unit, moving the ionized urine sample in vacuum and separating it according to the mass-to-charge ratio by using electromagnetic force or by the time-of-flight differences. As the method of ionization using an ion source, a method such as electron ionization (EI), chemical ionization (CI), field desorption/ionization (FD), fast atom bombardment ionization (FAB), matrix-assisted laser desorption/ionization (MALDI), and electrospray ionization (ESI) can be appropriately selected. Moreover, as the method for separating the ionized urine sample in the analysis unit, a separation method such as magnetic deflection, quadrupole, ion trap, time-of-flight (TOF), and Fourier transform ion cyclotron resonance can be appropriately selected. Tandem mass spectrometry (MS/MS), which combines two or more mass spectrometry methods, can also be used. In addition, 3',4'-didehydro-3'-deoxycytidine can be separated and purified for analysis from impurities by gas chromatography (GC), liquid chromatography (LC) or high performance liquid chromatography (HPLC).

In the present description, the urinary concentration of 3',4'-didehydro-3'-deoxycytidine may be an absolute or relative value. In the case of a relative value, examples thereof include a relative value based on 3',4'-didehydro-3'-deoxycytidine of a known concentration (internal standard) and a relative value based on the creatinine content in urine (for example, mg/g Cr).

(Step (b) in Detection Method of the Present Invention)

The above step (b) is not particularly limited as long as it is a step of comparing the concentration of 3',4'-didehydro-3'-deoxycytidine measured in step (a) with a reference concentration for control. In the present description, as the "reference concentration for control", the concentration of 3',4'-didehydro-3'-deoxycytidine in the urine collected from a person who does not have systemic lupus erythematosus (hereinafter, also indicated as "control person") can be used. The above control person should be a person who does not have systemic lupus erythematosus, and examples thereof include a person who does not have lupus nephritis, and a healthy individual, among which a patient with nephrotic syndrome whose form is not lupus nephritis and a healthy individual are preferably included, among which a patient with nephrotic syndrome whose form is not lupus nephritis is more preferably included. The above "patient with nephrotic syndrome whose form is not lupus nephritis" is not particularly limited as long as it is a patient with nephrotic syndrome whose form is not lupus nephritis, but preferably includes a patient having one or more (for example, three or more, four or more, five or more or six) forms of nephrotic syndrome selected from the group consisting of minimal change nephrotic syndrome (MCNS), membranous nephropathy (MN), diabetic nephropathy (DN), focal segmental glomerulosclerosis (FSGS), IgA nephropathy (IgA) and renal amyloidosis (RA). In addition, for the "concentration of 3',4'-didehydro-3'-deoxycytidine measured in step (a)" and the "reference concentration for control" (hereinafter, also collectively indicated as the "two concentrations"), it is preferable to use the corresponding concentrations. Specifically, it is preferable to use a concentration measured by substantially the same measurement method (method for preparing the urine sample from urine, method for measuring the concentration of 3',4'-didehydro-3'-deoxycytidine in the urine sample, etc.), except that the origin of urine is different. When an absolute value is used as one of the two concentrations, it is preferable to use an absolute value as the other concentration, and when a relative value is used as one of the two concentrations, it is preferable to use a relative value as the other concentration. For the above "reference concentration for control", a urine sample for analysis may be prepared from urine collected from a control person and measured each time the detection method of the present invention is performed, but a concentration measured beforehand may also be used.

A concentration of 3',4'-didehydro-3'-deoxycytidine in the urine collected from a test subject (for example, the concentration of 3',4'-didehydro-3'-deoxycytidine in urine measured in step (a)) (hereinafter, also indicated as "concentration in the test subject") higher than the reference concentration for control indicates a strong possibility that the test subject has systemic lupus erythematosus, and a concentration in the test subject equal to or lower (preferably lower) than the reference concentration for control indicates a low possibility that the test subject has systemic lupus erythematosus.

A threshold (cutoff value) can be set to determine whether or not the concentration in the test subject is higher than the reference concentration for control. Examples of this threshold include the "mean", "mean+standard deviation (SD)", "mean+2SD", and "mean+3SD" of the concentration in the control person; and the "median", "median+SD", "median+2SD", and "median+3SD" of the concentration in the control person. In addition, the threshold can also be calculated using a ROC (Receiver Operating Characteristic) curve using statistical analysis software based on the data of "concentrations in the test subject" and the data of "concentrations in the control person" to increase the sensitivity (proportion of those who have systemic lupus erythematosus (preferably lupus nephritis) who are correctly identified as positive, preferably the proportion of those whose form of nephrotic syndrome is lupus nephritis who are correctly identified as positive) and the specificity (proportion of those who do not have systemic lupus erythematosus (preferably lupus nephritis) who are correctly identified as negative, preferably the proportion of those whose form of nephrotic syndrome is not lupus nephritis who are correctly identified as negative).

In the detection method of the present invention and the biomarker for detection of the present invention, the case indicating a strong possibility that the test subject has systemic lupus erythematosus (preferably lupus nephritis) (preferably the possibility that the test subject's disease form is lupus nephritis) is not particularly limited as long as it is a case in which the concentration in the test subject is higher than the reference concentration for control, as described above, but preferably includes a case in which the concentration in the test subject is 1.2 times or more, preferably 1.6 times or more, more preferably 2 times or more, further preferably 2.5 times or more, more preferably 3 times or more, and further preferably 3.5 times or more than the reference concentration for control.

Moreover, in the detection method of the present invention and the biomarker for detection of the present invention, examples of other cases indicating a strong possibility that the test subject has systemic lupus erythematosus (preferably lupus nephritis) (preferably the possibility that the test subject's disease form is lupus nephritis) include a case in which the concentration in the test subject is 1.9 mg/g Cr or more, preferably 2.5 mg/g Cr or more, more preferably 3 mg/g Cr or more, further preferably 3.5 mg/g Cr or more, more preferably 4 mg/g Cr or more, and further preferably 5 mg/g Cr or more. These cases imply that 1.9 mg/g Cr, preferably 2.5 mg/g Cr, more preferably 3 mg/g Cr, further preferably 3.5 mg/g Cr, more preferably 4 mg/g Cr, and further preferably 5 mg/g Cr is used as the reference concentration for control.

(Step (A) in Method for Prognosis Prediction of the Present Invention)

The above step (A) is not particularly limited as long as it is a step of measuring the concentration of 3',4'-didehydro-3'-deoxycytidine in the urine collected from a patient already diagnosed with systemic lupus erythematosus, but the urine used herein is preferably collected from a patient before administering an immunosuppressive treatment. Moreover, in this step, the concentration of 3',4'-didehydro-3'-deoxycytidine can be measured by a publicly known method similar to the above-mentioned step (a).

In the method for prognosis prediction of the present invention, it can be predicted that the prognosis is good when the concentration of 3',4'-didehydro-3'-deoxycytidine obtained in the above step (A) is high. Here, a "good prognosis" means that the systemic symptoms or at least some of the organ lesions are in remission or low disease activity following treatment. For example, as described in the following Examples, when the concentration of 3',4'-didehydro-3'-deoxycytidine in the urine of a patient with systemic lupus erythematosus is 20 mg/g Cr or more, it can be predicted that there is a stronger possibility of complete remission 6 to 24 months after an immunosuppressive treatment, as compared with the case of a concentration of 20 mg/g Cr or less.

Note that "mg/g Cr" represents the weight (mg) of a substance (3',4'-didehydro-3'-deoxycytidine in the present invention) with respect to 1 g of creatinine.

(Kit of Present Invention)

The kit of the present invention is not particularly limited as long as it is a kit for detecting or predicting the prognosis of systemic lupus erythematosus, comprising 3',4'-didehydro-3'-deoxycytidine as an internal standard substance for a mass spectrometer, but it is preferable that 3',4'-didehydro-3'-deoxycytidine be isotopically labelled. Examples of isotope labeling include labeling with radioisotopes and labeling with elements such as carbon, nitrogen, oxygen, and deuterium, but labeling with deuterium is preferable. In addition, the kit of the present invention may further comprise an additional test reagent, a diluent, an instruction for use, and the like.

Other Embodiments of Present Invention

The present invention also includes the following embodiments:

a method for collecting data for detecting (or diagnosing) whether a test subject has systemic lupus erythematosus (preferably lupus nephritis), comprising:
(a) a step of measuring the concentration of 3',4'-didehydro-3'-deoxycytidine in urine collected from the test subject; and
(b) a step of comparing the concentration of 3',4'-didehydro-3'-deoxycytidine measured in step (a) with a reference concentration for control;

a method for assisting the diagnosis of whether a test subject has systemic lupus erythematosus (preferably lupus nephritis) (note that the method does not include the diagnostic action of a doctor), comprising:
(a) a step of measuring the concentration of 3',4'-didehydro-3'-deoxycytidine in urine collected from the test subject; and
(b) a step of comparing the concentration of 3',4'-didehydro-3'-deoxycytidine measured in step (a) with a reference concentration for control;

a method for diagnosing whether a test subject has systemic lupus erythematosus (preferably lupus nephritis), comprising:
(a) a step of measuring the concentration of 3',4'-didehydro-3'-deoxycytidine in urine collected from the test subject; and
(b) a step of comparing the concentration of 3',4'-didehydro-3'-deoxycytidine measured in step (a) with a reference concentration for control;

a method for diagnosing whether a test subject has systemic lupus erythematosus (preferably lupus nephritis), comprising:
(a) a step of measuring the concentration of 3',4'-didehydro-3'-deoxycytidine in urine collected from the test subject;
(b) a step of comparing the concentration of 3',4'-didehydro-3'-deoxycytidine measured in step (a) with a reference concentration for control; and (c) a step of administering a treatment for systemic lupus erythematosus (preferably lupus nephritis) to the test subject when the possibility that the test subject has systemic lupus erythematosus (preferably lupus nephritis) is strong, which is indicated by a concentration of 3',4'-didehydro-3'-deoxycytidine measured in step (a) higher than the reference concentration for control; and 3',4'-didehydro-3'-deoxycytidine for use in diagnosing whether a subject has systemic lupus erythematosus (preferably whether a subject has nephrotic syndrome, more preferably whether the form of nephrotic syndrome is lupus nephritis).

Hereinafter, the present invention will be more specifically described by Examples, but the technical scope of the present invention is not limited to these examples.

Example 1

1. Method

The following experiments were conducted to search for a biomarker capable of differentiating lupus nephritis among nephrotic syndrome with high accuracy.

[Urine Sample]

To search for a biomarker, the urine samples of 274 patients with nephrotic syndrome stored at Nagoya University Hospital were used. The patient information of these patients with nephrotic syndrome is shown in Table 1 below. Note that all of the 274 patients mentioned above have undergone renal biopsy, and that the form of disease has been confirmed.

flight mass spectrometer (CE-TOFMS). The measurement conditions for cationic metabolites are shown in (1) below, and the measurement conditions for anionic metabolites are shown in (2) below.

(1) Measurement Conditions for Cationic Metabolites

For the measurement conditions for cationic metabolites, the measurement conditions described in the following documents (s) and (t) were referred to.

(s) Soga, T., Ohashi, Y., Ueno, Y., Naraoka, H., Tomita, M., and Nishioka, T., "Quantitative Metabolome Analysis Using Capillary Electrophoresis Mass Spectrometry", J. Proteome Res. 2. 488-494, 2003.

(t) Soga, T., Baran, R., *Suematsu M., Ueno, Y., Ikeda, S., Sakurakawa T., Kakazu, Y., Ishikawa, T., Robert, M., Nishioka, T., Tomita, M., "Differential Metabolomics Reveals Ophthalmic Acid As An Oxidative Stress Biomarker Indicating Hepatic Glutathione Consumption", J. Biol. Chem. 281, 16768-16776, 2006.

The specific measurement conditions for cationic metabolites were as follows.

(1-1) Analytical Conditions for Capillary Electrophoresis (CE)

For the capillary, a fused silica capillary (inner diameter: 50 µm, outer diameter: 360 µm, total length: 100 cm) was used. A 1 M aqueous solution of formic acid (pH: about 1.8) was used for the buffer solution. The electrophoresis was performed with an applied voltage of +30 kV and a capillary temperature of 20° C. The urine sample for analysis was injected into one end of the capillary at 50 mbar for 3 seconds using a pressure method.

TABLE 1

| Disease | Abbreviation | Number of samples | Mean age (Minimum-Maximum) | Sex (Male/Female) | Average Estimated Glomerular Filtration Rate (Minimum-Maximum) |
|---|---|---|---|---|---|
| Membranous Nephropathy | MN | 78 | 63.8 (37-81) | 62/16 | 61.7 (9.8-88.5) |
| Diabetic Nephropathy | DN | 29 | 57.5 (29-78) | 22/7 | 35.2 (5.8-78.8) |
| Minimal Change Nephrotic Syndrome | MCNS | 74 | 57.2 (26-82) | 50/24 | 59.0 (14.1-89.3) |
| Lupus Nephritis | LN | 27 | 52.9 (27-80) | 6/21 | 48.5 (6.4-82.7) |
| Renal Amyloidosis | RA | 19 | 71.0 (51-86) | 15/4 | 45.0 (15.7-82.7) |
| Focal Segmental Glomerulosclerosis | FSGS | 29 | 58.5 (32-78) | 20/9 | 52.8 (16.7-81.9) |
| IgA Nephropathy | IgA | 18 | 56.1 (27-79) | 13/5 | 46.8 (5.4-90.0) |
| Total | | 274 | | | |

[Pretreatment of Urine Sample]

The concentration of urine samples varies relatively greatly depending on the timing of collection and individual differences. Therefore, in order to search for biomarkers in urine more accurately, the concentration of each urine sample was corrected by the creatinine concentration in urine. Specifically, the level of creatinine in each urine sample was quantified by a publicly known enzymatic method, and based on the results, each urine sample was diluted with water to obtain a final concentration of creatinine in each urine sample of 10 mg/dL. The diluted urine samples were subjected to mass spectrometry as described below.

[Analysis of Urinary Metabolites by Mass Spectrometer]

The analysis of urinary metabolites in each urine sample was performed using a capillary electrophoresis time-of- (1-2) Analytical Conditions for Time-Of-Flight Mass Spectrometer (TOFMS)

Using the positive ion mode, the ionization voltage was set to 4 kV, the fragmenter voltage to 75 V, the skimmer voltage to 50 V, and the OctRFV voltage to 125 V. Nitrogen was used as the dry gas, and the temperature of dry gas was set to 300° C. and the pressure to 10 psig. A 50% methanol solution was used for the sheath solution, to which hexakis (2,2-difluoroethoxy)phosphazene was mixed for mass calibration at 0.1 µM. The sheath solution was delivered at 10 µL/min. All data obtained in positive ion mode were automatically calibrated using the mass number of hexakis(2,2-difluoroethoxy)phosphazene (m/z: 622.0290) and the methanol dimer isotope (m/z: 66.0632).

(2) Measurement Conditions for Anionic Metabolites

For the measurement conditions for anionic metabolites, the measurement conditions described in the following document (u) were referred to. (u) Soga, T., Igarashi, K., Ito, T., Mizobuchi, K., Zimmermann, H., Tomita, M., "Metabolomic Profiling of Anionic Metabolites by Capillary Electrophoresis Mass Spectrometry", Anal. Chem. 81, 6165-6174, 2009.

(2-1) Analytical Conditions for Capillary Electrophoresis (CE)

For the capillary, a COSMO(+) capillary (inner diameter: 50 μm, outer diameter: 360 μm, total length: 100 cm) was used. A 50 mM aqueous solution of ammonium acetate (pH: 8.5) was used for the buffer solution. The electrophoresis was performed with an applied voltage of −30 kV and a capillary temperature of 20° C. The urine sample for analysis was injected into one end of the capillary at 50 mbar for 30 seconds using a pressure method.

(2-2) Analytical Conditions for Time-Of-Flight Mass Spectrometer (TOFMS)

Using the negative ion mode, the ionization voltage was set to 3.5 kV, the fragmenter voltage to 100 V, the skimmer voltage to 50 V, and the OctRFV voltage to 200 V. Nitrogen was used as the dry gas, and the temperature was set to 300° C. and the pressure to 10 psig. A 50% methanol solution containing 5 mM ammonium acetate was used for the sheath solution, to which hexakis(2,2-difluoroethoxy)phosphazene was mixed for mass calibration at 0.1 M. The sheath solution was delivered at 10 μL/min. All data obtained in negative ion mode were automatically calibrated using the mass number of the acetate adduct ion of hexakis(2,2-difluoroethoxy) phosphazene (m/z: 680.0355) and the acetic acid dimer isotope (m/z: 120.0384).

2. Results

[Search for Biomarker]

CE-TOFMS was performed by the method described above on the urine samples of the 274 patients with nephrotic syndrome described above, and followed by a metabolome analysis. As a result, a total of 220 metabolite peaks were detected in the urine of these patients with nephrotic syndrome. A statistical analysis was performed on all of the peaks of these urinary metabolites to search for marker candidates capable of detecting a strong possibility of being affected by one of the seven forms of nephrotic syndrome. As a result, a marker candidate peak (peak ID "CU040" (later identified as 3',4'-didehydro-3'-deoxycytidine) was found, which is capable of detecting a strong possibility of having lupus nephritis, which is one specific form among the seven forms of nephrotic syndrome. The minimum, 5th percentile, 25th percentile, 50th percentile (median), 75th percentile, 95th percentile, and maximum of the relative concentrations of CU040 in each form group of the seven forms of nephrotic syndrome are shown in Table 2, and the diagram representing these values in a box plot is shown in FIG. 1.

TABLE 2

| | MN | DN | MCNS | LN | RA | FSGS | IgA |
|---|---|---|---|---|---|---|---|
| Number of samples | 78 | 29 | 74 | 27 | 19 | 29 | 18 |
| Minimum | 2.417 | 0 | 1.726 | 0 | 3.323 | 2.428 | 3.429 |
| 5th percentile (lower end of whiskers) | 2.999 | 0.7917 | 2.265 | 1.234 | 3.323 | 2.772 | 3.429 |
| 25th percentile (bottom edge of box) | 4.231 | 4.587 | 3.639 | 10.13 | 4.321 | 4.798 | 4.471 |
| 50th percentile (partition line in box) | 5.752 | 6.172 | 5.343 | 23.59 | 6.625 | 6.321 | 5.545 |
| 75th percentile (top edge of box) | 7.287 | 13.11 | 6.784 | 51.26 | 12.29 | 7.426 | 9.176 |
| 95th percentile (upper end of whiskers) | 15.20 | 34.60 | 10.46 | 246.7 | 18.33 | 46.46 | 17.94 |
| Maximum | 36.77 | 36.92 | 21.83 | 295.4 | 18.33 | 82.53 | 17.94 |

As evident from the results of FIG. 1, of the seven forms of nephrotic syndrome, the relative concentration of the peak ID "CU040" (3',4'-didehydro-3'-deoxycytidine) only showed a high value for lupus nephritis (LN). For example, when compared at the 50th percentile, the relative concentration in the form lupus nephritis was at least 3.56 times or more than the relative concentration in the other forms.

Based on the relative concentrations of CU040 (3',4'-didehydro-3'-deoxycytidine) in the urine samples of the lupus nephritis group and the relative concentrations of CU040 in the urine samples of the six disease form groups other than lupus nephritis, a ROC curve was created, which showed a high AUC value of 0.8218 (FIG. 2). In addition, when 18.398 was set as the cutoff value of the relative concentration of CU040 to distinguish the lupus nephritis group, which is a form of nephrotic syndrome, from the other six disease form groups of nephrotic syndrome, the sensitivity of patients with nephrotic syndrome having lupus nephritis (that is, the proportion of patients with lupus nephritis who are tested positive) and the specificity (the proportion of patients with nephrotic syndrome who do not have lupus nephritis who are tested negative) were 0.7037 (70.37%) and 0.9717 (97.17%), respectively.

These results show that when the relative concentration of 3',4'-didehydro-3'-deoxycytidine in urine collected from patients with nephrotic syndrome is measured and an appropriate cutoff value is set, the possibility that the form of nephrotic syndrome is lupus nephritis can be detected with high accuracy using the concentration of 3',4'-didehydro-3'-deoxycytidine as an indicator. In addition, since lupus nephritis is a renal disorder caused by systemic lupus erythematosus, these results also showed that the possibility that a test subject has lupus nephritis, and further, the possibility that the subject has systemic lupus erythematosus can be detected with high accuracy using the concentration of 3',4'-didehydro-3'-deoxycytidine described above.

[Identification of CU040]

As described above, the peak ID "CU040" was an unknown peak at the beginning of the measurement since there was no corresponding standard reagent. To identify the substance of this peak, several liters of urine were collected by collecting urine from patients with systemic lupus erythematosus who do not have lupus nephritis, to attempt the recovery of the metabolite by preparative liquid chromatography and the identification of the substance by nuclear magnetic resonance. Since the composition formula of the metabolite (3',4'-didehydro-3'-deoxycytidine) reported to be detected in mouse urine in past literature (Tritten, L., Keiser, J., Godejohann, M., Utzinger, J., Vargas, M., Beckonert, O., Holmes, E., Saric, J., "Metabolic Profiling Framework for Discovery of Candidate Diagnostic Markers of Malaria", Scientific Rep. 3, 2769, 2013) was the same as the composition formula of CU040, the metabolite was synthesized and the peak of the synthetic metabolite ("KAH51-57") was compared with the peak of CU040. The results are shown in FIGS. 3A-3F.

As evident from the results of FIGS. 3A-3F, the synthetic metabolite and CU040 had the same peak retention time and the same major MS/MS (tandem mass) spectra. Therefore, CU040 was identified as 3',4'-didehydro-3'-deoxycytidine. These results showed that CU040 is also contained in the urine of patients with systemic lupus erythematosus without nephritis.

[Calculation of Cut-Off Value for Diagnosing Systemic Lupus Erythematosus and Lupus Nephritis]

By the method described above, CE-TOFMS and a metabolome analysis were performed on the urine samples of 531 patients with or without nephrotic syndrome, composed of the seven disease forms described above including some of the 274 patients with nephrotic syndrome described above, and 15 healthy individuals for a total of 546 urine samples, as shown in Table 3. The results revealed the concentration distribution of CU040 in each group of the seven disease forms and healthy controls. The minimum, 10th percentile, 25th percentile, 50th percentile (median), 75th percentile, 90th percentile, and maximum of the concentrations of CU040 in each of the seven disease form groups and the healthy controls are shown in Table 4, and the diagram representing these values in a dot plot and a box plot is shown in FIG. 4.

TABLE 3

| Disease | Abbreviation | Number of samples | Age (years) (Median [25-75% quartile]) | Sex (Male/Female) | Estimated Glomerular Filtration Rate (Median [25-75% quartile]) | Urinary Protein Level (g/g Creatinine) (Median [25-75% quartile]) |
|---|---|---|---|---|---|---|
| Membranous Nephropathy | MN | 98 | 66 [61-73] | 66/32 | 72.0 [56.3-81.4] | 5.2 [3.2-9.1] |
| Diabetic Nephropathy | DN | 27 | 59 [50-65] | 18/9 | 35.6 [22.7-57.7] | 6.4 [3.1-9.5] |
| Minimal Change Nephrotic Syndrome | MCNS | 73 | 46 [35-56] | 44/29 | 72.0 [59.0-85.8] | 5.7 [3.2-8.8] |
| Lupus Nephritis | LN | 56 | 43 [33-59] | 16/40 | 70.4 [48.3-98.8] | 2.8 [1.0-6.6] |
| Renal Amyloidosis | RA | 20 | 70 [65-75] | 12/8 | 50.8 [32.7-56.6] | 4.8 [1.8-6.7] |
| Focal Segmental Glomerulosclerosis | FSGS | 16 | 65 [42-68] | 10/6 | 55.5 [40.7-63.4] | 2.1 [1.5-3.1] |
| IgA Nephropathy | IgA | 241 | 36 [27-49] | 110/131 | 68.3 [53.9-90.0] | 1.2 [0.8-2.1] |
| Healthy Control | HC | 15 | 38 [33-47] | 11/4 | — | — |
| Total | | 546 | | | | |

TABLE 4

|  | MN | DN | MCNS | LN | RA | FSGS | IgA | HC |
|---|---|---|---|---|---|---|---|---|
| Minimum | 0.00 | 0.26 | 0.00 | 0.21 | 0.00 | 0.00 | 0.00 | 0.29 |
| 10th percentile | 0.17 | 0.34 | 0.27 | 0.92 | 0.32 | 0.22 | 0.34 | 0.30 |
| 25th percentile | 0.48 | 0.48 | 0.42 | 2.45 | 0.53 | 0.39 | 0.41 | 0.36 |
| Median | 0.66 | 0.75 | 0.56 | 4.15 | 0.71 | 0.59 | 0.51 | 0.41 |
| 75th percentile | 1.00 | 1.00 | 0.95 | 8.00 | 1.28 | 0.83 | 0.66 | 0.63 |
| 90th percentile | 1.51 | 1.32 | 1.70 | 16.30 | 1.80 | 1.83 | 0.90 | 0.90 |
| Maximum | 4.50 | 2.10 | 5.20 | 37.00 | 2.00 | 3.30 | 3.90 | 1.07 |

(Unit = g CU040/g Creatinine)

Based on the concentrations of CU040 (3',4'-didehydro-3'-deoxycytidine) in the urine samples of the lupus nephritis group and the concentrations of CU040 in the urine samples of the six disease form groups other than lupus nephritis and the healthy controls, a ROC curve was created, which showed a high AUC value of 0.927 (FIG. 5). In addition, when 1.9 mg/g Cr was set as the cutoff value of the concentration of CU040 to distinguish the lupus nephritis group from the other six disease form groups and the healthy controls, the sensitivity of patients having lupus nephritis (that is, the proportion of patients with lupus nephritis who are tested positive) among the 531 patients with or without nephrotic syndrome, to which urine samples of 15 healthy individuals were added for a total of 546 subjects, and the specificity (that is, the proportion of patients with nephrotic syndrome who do not have lupus nephritis who are tested negative) were 0.8571 (85.71%) and 0.9612 (96.12%), respectively.

The results in Table 4, FIG. 4 and FIG. 5 show that when the concentration of 3',4'-didehydro-3'-deoxycytidine in urine collected from a test subject (whether a patient with nephrotic syndrome or not) is measured and an appropriate cutoff value is set, the possibility that the test subject from which the urine specimen was collected has lupus nephritis can be detected with high accuracy using the concentration of 3',4'-didehydro-3'-deoxycytidine as an indicator. The results described above in Table 4, FIG. 4 and FIG. 5 also show that when the concentration of 3',4'-didehydro-3'-deoxycytidine in urine collected from patients with nephrotic syndrome is measured and an appropriate cutoff value is set, the possibility that the disease form of the test subject from which the urine specimen was collected has lupus nephritis can be detected with high accuracy using the concentration of 3',4'-didehydro-3'-deoxycytidine as an indicator. In addition, since lupus nephritis is a renal disorder caused by systemic lupus erythematosus, these results also showed that the possibility that a test subject has lupus nephritis, and further, the possibility that the subject has systemic lupus erythematosus can be detected with high accuracy using the concentration of 3',4'-didehydro-3'-deoxycytidine described above.

Example 2

[Correlation Analysis Between Urinary CU040 Concentration and Clinical Parameters]

The correlation between the urinary concentration of CU040 (3',4'-didehydro-3'-deoxycytidine) in patients with nephrotic syndrome and various clinical parameters was investigated. Specifically, the concentration of 3',4'-didehydro-3'-deoxycytidine in urine samples (n=63) collected from patients with nephrotic syndrome was quantified by the method described in Example 1. The patient distribution number was analyzed based on the obtained urinary 3',4'-didehydro-3'-deoxycytidine concentrations. First, as a result of examining the patient distribution number at nine ranges of 3',4'-didehydro-3'-deoxycytidine concentration, the number of patients having a concentration of less than 10 mg/g Cr was 19, the number of patients having a concentration of 10 to 20 mg/g Cr was 16, the number of patients having a concentration of 20 to 30 mg/g Cr was 17, the number of patients having a concentration of 30 to 40 mg/g Cr was 7, the number of patients having a concentration of 40 to 50 mg/g Cr was 3, and the number of patients having a concentration of 90 to 100 mg/g Cr was 1 (upper graph in FIG. 6). Based on these results, the patient distribution number was further examined at four ranges of 3',4'-didehydro-3'-deoxycytidine concentration, and as a result, the number of patients having a concentration of less than 10 mg/g Cr was 19, the number of patients having a concentration of 10 to 20 mg/g Cr was 16, the number of patients having a concentration of 20 to 30 mg/g Cr was 17, and the number of patients having a concentration of 30 mg/g Cr or more was 11 (lower graph in FIG. 6).

Figure 7:
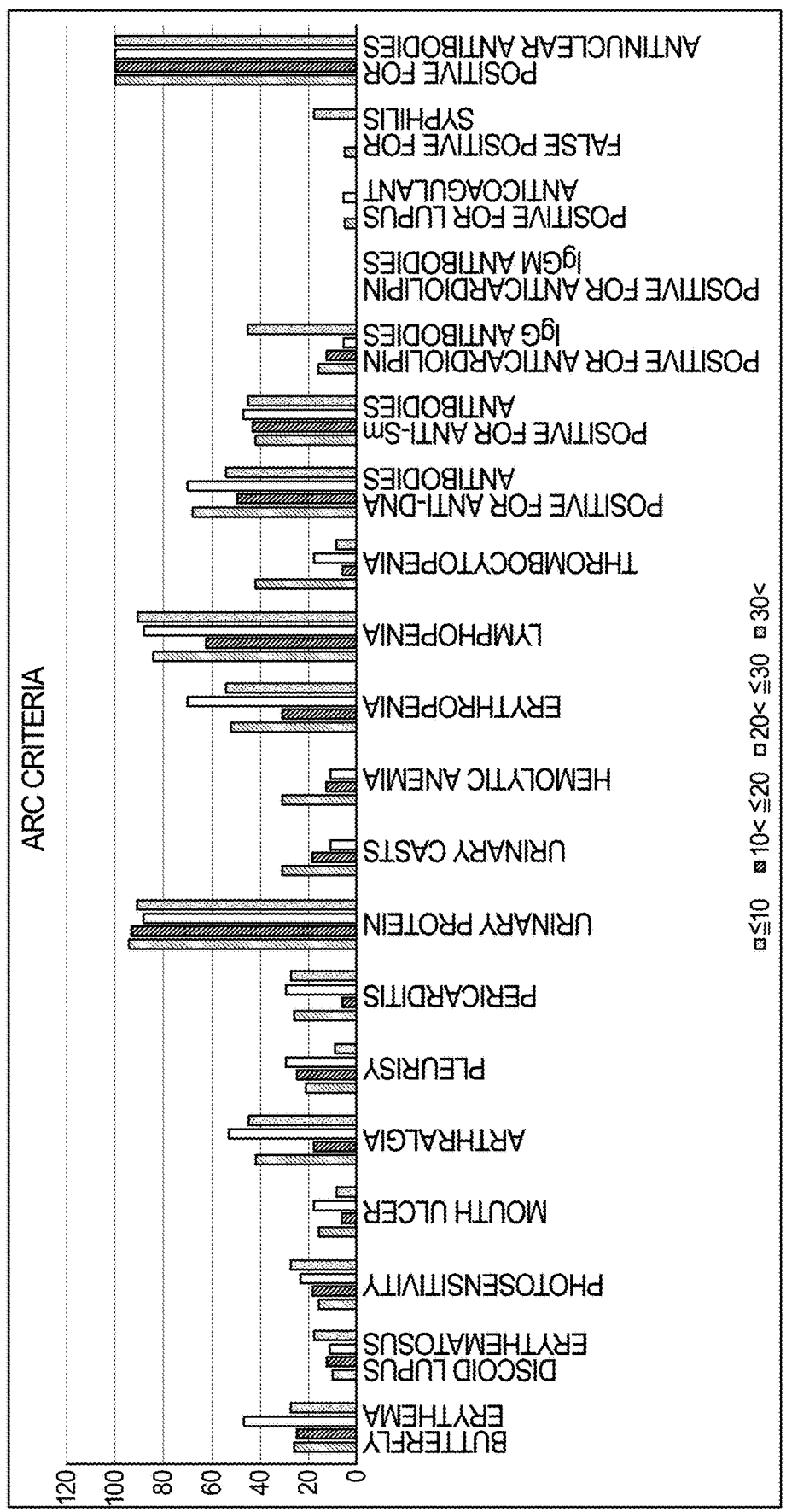
FIG. 7 is a diagram showing the relationship between urinary CU040 concentration and the American College of Rheumatology (ARC) criteria. The vertical axis indicates the ratio (%) of number of patients belonging to a CU040 concentration range who fall under an ARC criterion, and the horizontal axis indicates each ARC criterion. The graphs for each ARC criterion on the horizontal axis show, from the left, the results of "≤10", "10< ≤20", "20< ≤30", and "30<", respectively.
Figure 8:
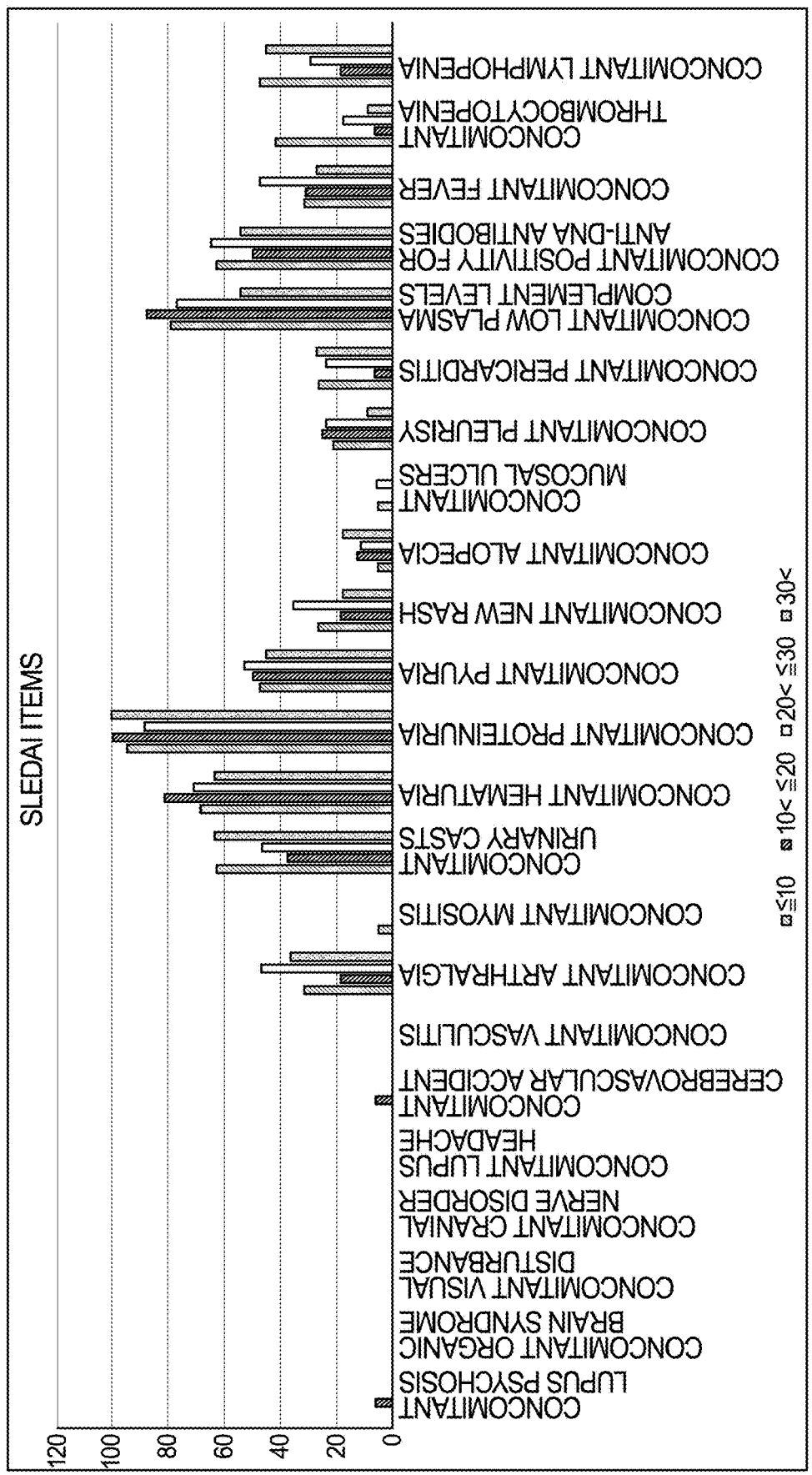
FIG. 8 is a diagram showing the relationship between urinary CU040 concentration and SLE disease activity index (SLEDAI). The vertical axis indicates the ratio (%) of number of patients belonging to a CU040 concentration range who fall under an ARC criterion, and the horizontal axis indicates each SLEDAI item. The graphs for each SLEDAI item on the horizontal axis show, from the left, the results of "≤10", "10< ≤20", "20< ≤30", and "30<", respectively.

Next, the clinical parameters for each of the patient groups classified into the above four ranges were analyzed and made into a graph. As the clinical parameters, the American College of Rheumatology (ARC) criteria and the SLE disease activity index (SLEDAI) were used. The correlation between each parameter and the urinary 3',4'-didehydro-3'-deoxycytidine concentration is shown in FIGS. 7 and 8. As shown in FIGS. 7 and 8, correlations with some clinical parameters were observed in the 3',4'-didehydro-3'-deoxycytidine high concentration range. As the concentration of 3',4'-didehydro-3'-deoxycytidine increased, the scores for discoid lupus erythematosus, photosensitivity, and concomitant alopecia showed a tendency to increase, and conversely, the scores for urinary casts and hemolytic anemia showed a tendency to decrease.

Example 3

[Relationship Between Urinary CU040 Concentration and Prognosis of Systemic Lupus Erythematosus]

Urine samples were collected from patients with systemic lupus erythematosus who had undergone renal biopsy at the Department of Nephrology of Nagoya University, and the CU040 (3',4'-didehydro-3'-deoxycytidine) concentration in the urine samples was measured. These CU040 concentrations were calculated by measuring the concentrations in the urine samples with CE-MS and then correcting them with the creatinine concentrations in the urine samples.

These patients with systemic lupus erythematosus were divided into two groups: urinary 3',4'-didehydro-3'-deoxycytidine concentration of less than 20 mg/g Cr (n=30) and of 20 mg/g Cr or more (n=27), and the rates of complete remission 3, 6, 12 and 24 months after an immunosuppressive treatment were compared. The time at which the urinary protein levels dropped to 0.2 g/day or less was considered as complete remission. The results of comparing the rates of complete remission are shown in Table 5 and FIG. 9. Of the two graphs in FIG. 9, the graph with a generally high cumulative rate of achieving first complete remission represents the result for "CU040 20=<", and the graph with a generally low cumulative rate of achieving first complete remission represents the result for "CU040 <20".

TABLE 5

Table. Percentage of patients who reached complete remission

| CU040 Concentration | | ≤20 (N = 30) | 20< (N = 27) | P value |
|---|---|---|---|---|
| Complete Remission | Within 3 months | 7 (23) | 12 (44) | 0.091 |
| | Within 6 months | 9 (30) | 16 (59) | 0.026 |
| | Within 12 months | 12 (40) | 18 (67) | 0.044 |
| | Within 24 months | 13 (43) | 20 (74) | 0.019 |

57 patients who could be determined as having reached complete remission

Figure 9:
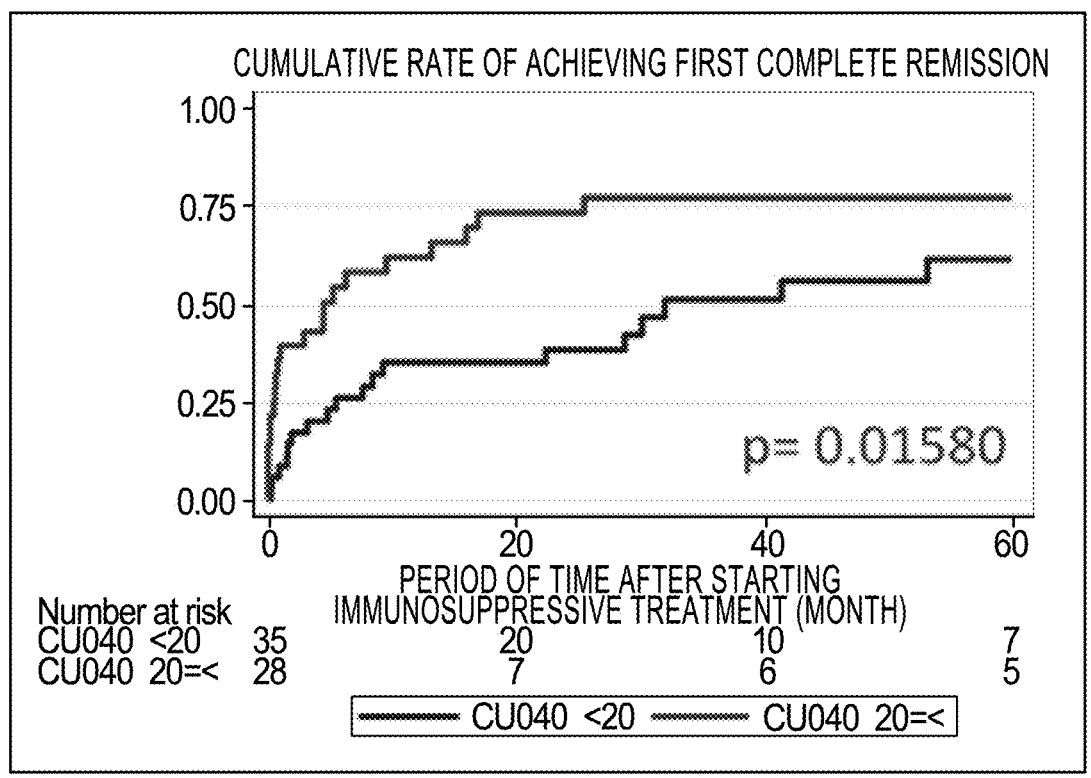
FIG. 9 is a diagram showing the relationship between urinary CU040 concentration and prognosis in patients with nephrotic syndrome. Of the two graphs in FIG. 9, the graph with a generally high cumulative rate of achieving first complete remission represents the result for "CU040 20=<", and the graph with a generally low cumulative rate of achieving first complete remission represents the result for "CU040 <20".

As shown in Table 5 and FIG. 9, at 6, 12, and 24 months after immunosuppressive treatment, significantly higher rates of complete remission were observed in the group having a urinary 3',4'-didehydro-3'-deoxycytidine concentration of 20 mg/g Cr or more than in the group having a urinary 3',4'-didehydro-3'-deoxycytidine concentration of less than 20 mg/g Cr. These results suggest that the urinary 3',4'-didehydro-3'-deoxycytidine concentration can be used as a biomarker for prognosis estimation.

INDUSTRIAL APPLICABILITY

According to the present invention, a method capable of detecting systemic lupus erythematosus with high accuracy, a method capable of detecting whether the form of nephrotic syndrome is lupus nephritis with high accuracy without performing a renal biopsy, a biomarker for carrying out such detections, and the like can be provided.

The invention claimed is:

1. A method for treating systemic lupus erythematosus, comprising:
   (a) a step of measuring the concentration of 3',4'-didehydro-3'-deoxycytidine in urine collected from a test subject;
   (b) a step of comparing the concentration of 3',4'-didehydro-3'-deoxycytidine measured in step (a) with a reference concentration for control;
   (c) a step of diagnosing the test subject as having systemic lupus erythematosus wherein
   the concentration of 3',4'-didehydro-3'-deoxycytidine measured in the step (a) is higher than the reference concentration for control; and
   (d) a step of administering an immunosuppressive treatment to the test subject diagnosed with system lupus erythematosus.

2. The treatment method according to claim 1, wherein when the concentration of 3',4'-didehydro-3'-deoxycytidine measured in step (a) is 1.2 times or more than the reference concentration for control, the test subject is diagnosed as having systemic lupus erythematosus.

3. The treatment method according to claim 1, wherein the reference concentration for control is the concentration of 3',4'-didehydro-3'-deoxycytidine in urine collected from a patient with nephrotic syndrome of a form other than lupus nephritis or from a healthy individual.

4. The treatment method according to claim 2, wherein the reference concentration for control is the concentration of 3',4'-didehydro-3'-deoxycytidine in urine collected from a patient with nephrotic syndrome of a form other than lupus nephritis or from a healthy individual.

5. The treatment method according to claim 1, wherein the test subject is a patient with is lupus nephritis.

6. The treatment method according to claim 2, wherein the test subject is a patient with is lupus nephritis.

7. The treatment method according to claim 3, wherein the test subject is a patient with is lupus nephritis.

8. The treatment method according to claim 4, wherein the test subject is a patient with is lupus nephritis.

9. A method for treating systemic lupus erythematosus, comprising:
   (A) a step of measuring a concentration of 3',4'-didehydro-3'-deoxycytidine that is 20 mg/g or more with respect to 1 g of creatine in urine collected from a patient with systemic lupus erythematosus;
   (B) a step of diagnosing the patient with systemic lupus erythematosus as having a possibility of complete remission 6 to 24 months after an immunosuppressive treatment; and
   (C) a step of administering an immunosuppressive treatment to the patient with systemic lupus erythematosus diagnosed as having the possibility of complete remission 6 to 24 months after an immunosuppressive treatment.

* * * * *